US012734350B2

(12) United States Patent
Hansen

(10) Patent No.: US 12,734,350 B2
(45) Date of Patent: Sep. 15, 2026

(54) EXTRACORPOREAL BLOOD PUMP ASSEMBLY AND METHODS OF ASSEMBLING SAME

(71) Applicant: TC1 LLC, St. Paul, MN (US)

(72) Inventor: John Freddy Hansen, Livermore, CA (US)

(73) Assignee: TC1 LLC, St. Paul, MN (US)

(*) Notice: Subject to any disclaimer, the term of this patent is extended or adjusted under 35 U.S.C. 154(b) by 1005 days.

(21) Appl. No.: 17/303,877

(22) Filed: Jun. 9, 2021

(65) Prior Publication Data

US 2021/0393941 A1 Dec. 23, 2021

Related U.S. Application Data

(60) Provisional application No. 63/040,307, filed on Jun. 17, 2020.

(51) Int. Cl.
*A61M 60/109* (2021.01)
*A61M 1/16* (2006.01)
(Continued)

(52) U.S. Cl.
CPC ........ *A61M 60/109* (2021.01); *A61M 1/1698* (2013.01); *A61M 60/237* (2021.01);
(Continued)

(58) Field of Classification Search
CPC .............. A61M 1/3667; A61M 1/1698; A61M 223/04; A61M 1/3659; A61M 60/109; A61M 60/237; A61M 60/38; A61M 60/812; A61M 1/3623; A61M 2205/3606; A61M 2205/3653; A61M 2205/3673; A61M 2207/00; A61M 1/3666; A61M 60/226; A61M 60/232; A61M 60/422; A61M 60/81
See application file for complete search history.

(56) References Cited

U.S. PATENT DOCUMENTS 4,659,549 A * 4/1987 Hamada ................ B01D 63/02 422/48
4,975,247 A 12/1990 Badolato et al.
(Continued)

FOREIGN PATENT DOCUMENTS

WO 2016161114 A1 10/2016

OTHER PUBLICATIONS

International Search Report and Written Opinion for International Application No. PCT/US2021/036646, mailed Sep. 21, 2021, 12 pages.

*Primary Examiner* — Catharine L Anderson
*Assistant Examiner* — Nhu Q. Tran
(74) *Attorney, Agent, or Firm* — Armstrong Teasdale LLP

(57) ABSTRACT

An extracorporeal blood pump assembly includes a blood pump and an extracorporeal membrane oxygenator (ECMO). The blood pump includes a pump housing, a rotor, and a flow converter positioned downstream from the rotor to convert non-axial flow from the rotor to axial flow. The pump housing defines an inlet and an outlet. The ECMO includes a membrane housing and an oxygenator membrane disposed within the membrane housing. The membrane housing is removably connected to the pump housing at one of the pump housing inlet and the pump housing outlet.

18 Claims, 9 Drawing Sheets

(51) Int. Cl.
*A61M 1/36* (2006.01)
*A61M 60/237* (2021.01)
*A61M 60/38* (2021.01)
*A61M 60/812* (2021.01)

(52) U.S. Cl.
CPC .......... *A61M 60/38* (2021.01); *A61M 60/812* (2021.01); *A61M 1/3623* (2022.05); *A61M 2205/3606* (2013.01); *A61M 2205/3653* (2013.01); *A61M 2205/3673* (2013.01); *A61M 2207/00* (2013.01)

(56) References Cited

U.S. PATENT DOCUMENTS

| | | | | |
|---|---|---|---|---|
| 5,263,924 | A | 11/1993 | Mathewson | |
| 5,270,005 | A | 12/1993 | Raible | |
| 5,391,142 | A | 2/1995 | Sites et al. | |
| 5,429,486 | A | 7/1995 | Schock et al. | |
| 5,527,159 | A * | 6/1996 | Bozeman, Jr. | A61M 60/422 417/244 |
| 6,387,037 | B1 | 5/2002 | Bolling et al. | |
| 6,730,267 | B2 | 5/2004 | Stringer et al. | |
| 7,798,952 | B2 | 9/2010 | Tansley et al. | |
| 8,313,282 | B1 * | 11/2012 | Jarrah | F04D 13/026 165/80.4 |
| 8,496,874 | B2 | 7/2013 | Gellman et al. | |
| 8,770,945 | B2 | 7/2014 | Ozaki et al. | |
| 9,068,572 | B2 | 6/2015 | Ozaki et al. | |
| 9,091,271 | B2 | 7/2015 | Bourque | |
| 9,265,870 | B2 | 2/2016 | Reichenbach et al. | |
| 9,849,224 | B2 | 12/2017 | Angwin et al. | |
| 10,258,729 | B2 | 4/2019 | Gellman et al. | |
| 10,322,222 | B2 | 6/2019 | Peticca et al. | |
| 2003/0164333 | A1 * | 9/2003 | Nohren, Jr. | B01D 61/10 210/650 |
| 2008/0199357 | A1 * | 8/2008 | Gellman | A61M 1/3623 604/6.14 |
| 2016/0144089 | A1 * | 5/2016 | Woo | F04D 29/047 417/423.1 |
| 2019/0209760 | A1 * | 7/2019 | Simundic | A61M 60/221 |
| 2019/0247564 | A1 | 8/2019 | Lu et al. | |
| 2020/0237989 | A1 * | 7/2020 | Krivitski | A61M 1/1607 |
| 2020/0330669 | A1 * | 10/2020 | Kido | A61M 1/3673 |
| 2022/0280703 | A1 * | 9/2022 | Bonczar | A61M 60/113 |

* cited by examiner

EXTRACORPOREAL BLOOD PUMP ASSEMBLY AND METHODS OF ASSEMBLING SAME

BACKGROUND OF THE DISCLOSURE

This application claims priority to U.S. Provisional Patent Application Ser. No. 63/040,307, filed Jun. 17, 2020, the disclosure of which is hereby incorporated by reference in its entirety.

BACKGROUND OF THE DISCLOSURE a. Field of the Disclosure

The present disclosure relates generally to mechanical circulatory support systems, and more specifically relates to extracorporeal blood pump assemblies that include a combined blood pump and oxygenator.

b. Background

Many types of cardiac assist devices have been developed for applications in which a patient's heart is incapable of providing adequate circulation, commonly referred to as heart failure or congestive heart failure. For example, a patient suffering from chronic heart failure may use a ventricular assist device or VAD that is implanted in the patient while awaiting a heart transplant or as a long term destination therapy. As another example, a patient suffering from acute heart failure may use an extracorporeal pump or circulatory support system that pumps blood out and back into a patient's body. Extracorporeal circulatory support systems may also be used perioperatively, for example, to direct blood through a patient while surgery is performed on the heart.

At least some extracorporeal circulatory support systems temporarily replace a patient's heart and lung functions by pumping blood around or bypassing the patient's heart and lungs. Such extracorporeal circulatory support systems will typically include an oxygenator, such as an extracorporeal membrane oxygenator or ECMO, to provide oxygen to the blood passing through extracorporeal circulatory support system.

At least some extracorporeal circulatory support systems utilize an ECMO unit separate from the blood pump. The design of such extracorporeal circulatory support systems can result in a relatively large, combined pressure drop across the separate units, for example, due to the connections between the pump and ECMO unit and associated changes in cross-sectional area of the inlets and outlets of the respective units. Such pressure drops can be associated with or result in regions of turbulent blood flow or hemolysis.

Accordingly, a need exists for extracorporeal circulatory support systems that provide improved blood flow through the pump and oxygenator.

SUMMARY OF THE DISCLOSURE

The present disclosure is directed to an extracorporeal blood pump assembly that includes a blood pump and an extracorporeal membrane oxygenator (ECMO). The blood pump includes a pump housing, a rotor, and a flow converter positioned downstream from the rotor to convert non-axial flow from the rotor to axial flow. The pump housing defines an inlet and an outlet. The ECMO includes a membrane housing and an oxygenator membrane disposed within the membrane housing. The membrane housing is removably connected to the pump housing at one of the pump housing inlet and the pump housing outlet.

The present disclosure is also directed to an extracorporeal blood pump assembly kit that includes a blood pump, a first extracorporeal membrane oxygenator (ECMO), and a second ECMO. The blood pump includes a pump housing, a rotor, and a flow converter positioned downstream from the rotor to convert non-axial flow from the rotor to axial flow. The pump housing defines an inlet and an outlet. The first ECMO is removably connectable to one of the pump housing inlet and the pump housing outlet, and the second ECMO is removably connectable to the one of the pump housing inlet and the pump housing outlet such that the first ECMO is interchangeable with the second ECMO. The second ECMO has at least one of a size, a volume, and a gas exchange characteristic different from the first ECMO.

The present disclosure is further directed to a method of assembling an extracorporeal blood pump assembly. The method includes providing a blood pump including a pump housing, a rotor, and a flow converter positioned downstream from the rotor to convert non-axial flow from the rotor to axial flow. The pump housing defines an inlet and an outlet. The method further includes providing an extracorporeal membrane oxygenator (ECMO) that includes a membrane housing and an oxygenator membrane disposed within the membrane housing. The method further includes removably connecting the membrane housing to the pump housing at one of the pump housing inlet and the pump housing outlet.

DETAILED DESCRIPTION OF THE DISCLOSURE

The present disclosure is directed to mechanical circulatory support systems, and more specifically, to extracorporeal blood pump assemblies that include a combined blood pump and oxygenator. Embodiments of the extracorporeal blood pump assemblies disclosed herein include an integrated blood pump and an extracorporeal membrane oxygenator (ECMO). The design and configuration of the extracorporeal blood pump assemblies of the present disclosure facilitate reducing drops in blood pressure as compared, for example, to separate or standalone blood pump and ECMO modules. For example, embodiments of the blood pump assemblies provide a blood flow path that is free of bends and turns and that has a substantially constant cross-sectional area through the blood pump and the ECMO, thereby reducing or eliminating the nozzle/throat effect that otherwise results from connecting separate blood pump and ECMO modules with a piece of tubing. Embodiments of the blood pump assemblies may also be free of volutes, which might otherwise cause a nozzle/throat effect, a longer than necessary blood flow path (and associated pressure drop and larger priming volume), and at least one extra bend in the blood flow path.

Blood pump assemblies of the present disclosure also facilitate reducing the priming volume of the unit, for example, by eliminating tubing between the blood pump and the ECMO module and by providing modularity for different sized ECMO modules (e.g., ECMO modules for adult and pediatric modules with different priming volumes can be interchanged, as needed). The modularity of the blood pump assemblies also allows the oxygenator membrane of the ECMO to be replaced or discarded without having to discard the blood pump, allowing the blood pump to be cleaned and reused. Embodiments of the blood pump assemblies may also include an integrated heat exchanger, thereby eliminating the need for a separate heat exchanger and associated fluid lines (e.g., to connect separate water heater/water cooler).

Figure 1:
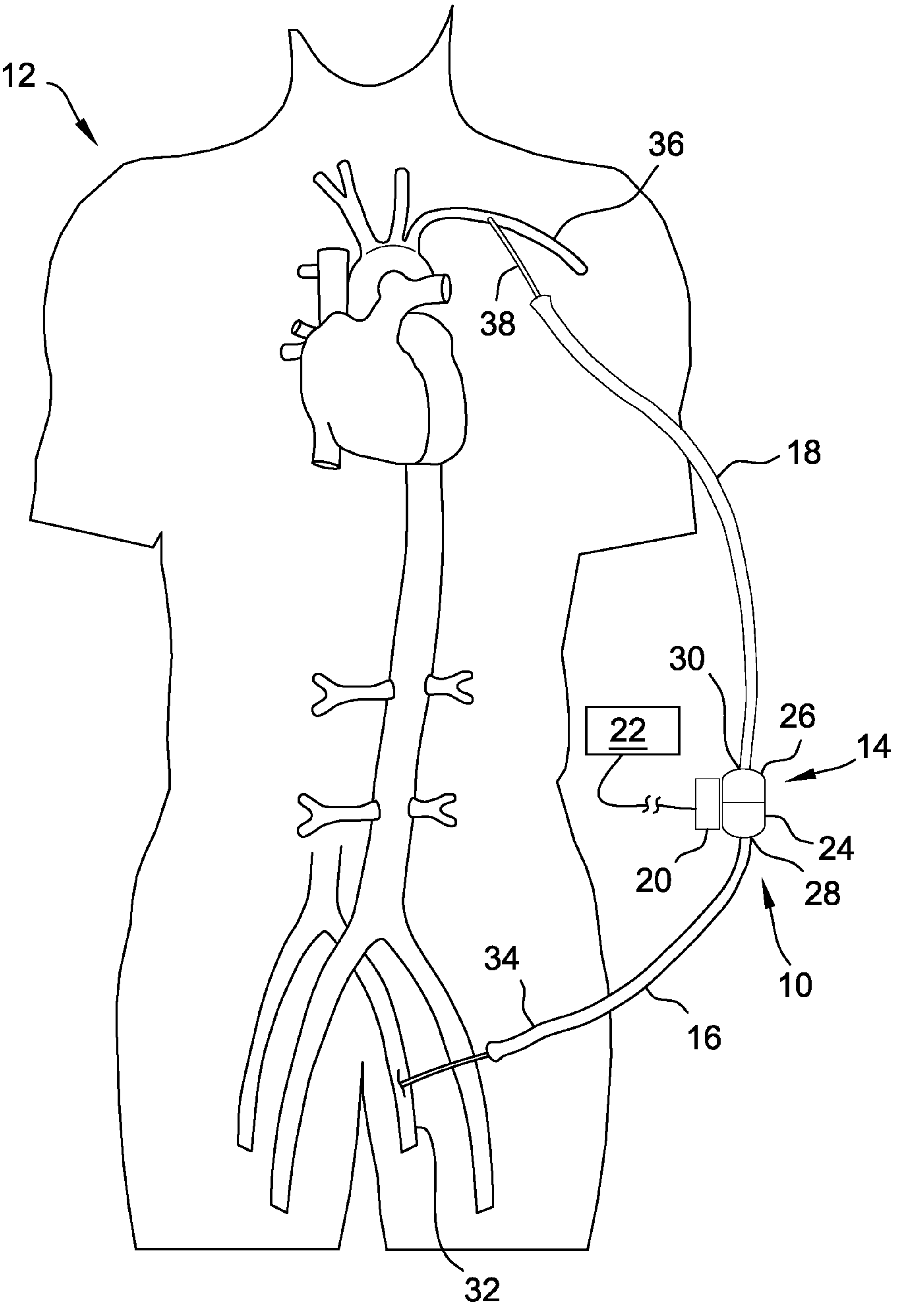
FIG. 1 is an illustration of an extracorporeal circulatory support system connected to a patient's body.

Referring now to the drawings, FIG. 1 is an illustration of an extracorporeal mechanical circulatory support system 10 connected a patient's 12 vasculature. The extracorporeal mechanical circulatory support system 10 includes an extracorporeal blood pump assembly 14, an inflow or first conduit 16, an outflow or second conduit 18, a controller 20, and a power supply 22.

The blood pump assembly 14 includes a blood pump 24, an extracorporeal membrane oxygenator (ECMO) 26, and an inlet 28 and an outlet 30 for connection of flexible conduits thereto. The blood pump assembly 14 may include any suitable type of pump that enables the blood pump assembly 14 to function as described herein, including, for example and without limitation, an axial rotary pump and a centrifugal rotary pump. The ECMO 26 includes an oxygenator membrane (not shown in FIG. 1) configured to increase the oxygen concentration and/or decrease the carbon dioxide concentration of blood pumped through the blood pump assembly 14. The oxygenator membrane may include any suitable type of oxygenator membrane that enables the blood pump assembly 14 to function as described herein including, for example and without limitation, fiber bundles. In some embodiments, the system 10 also includes a purge valve (not shown in FIG. 1) to release air or other gases present within the system 10. The purge valve can be connected, for example, to the outflow conduit 18, or may be integrated within the ECMO 26 (e.g., at an outlet of the ECMO 26).

The blood pump assembly 14 is connected to the patient's vasculature through the inflow conduit 16 and the outflow conduit 18. More specifically, the inlet 28 of the blood pump assembly 14 is connected to the inflow conduit 16, and the outlet 30 of the blood pump assembly 14 is connected to the outflow conduit 18. The inflow conduit 16 is connected to the patient's vasculature, specifically, to a first peripheral blood vessel 32 in the illustrated embodiment, by way of a first cannula 34, and the outflow conduit 18 is connected to the patient's vasculature, specifically, a second peripheral blood vessel 36 by way of a second cannula 38. The blood pump assembly 14 pumps blood from the first peripheral blood vessel 32, through the inflow conduit 16, through the blood pump assembly 14, and back into the second peripheral blood vessel 36 through the outflow conduit 18. In the illustrated embodiment, the first peripheral blood vessel 32 is a femoral vein, and the second peripheral blood vessel 36 is an axillary artery. It will be understood that the illustrated connections to the patient's vasculature are for illustrative purposes only, and that the blood pump assembly 14 may be connected to the patient's vasculature in any other suitable manner that enables that extracorporeal mechanical circulatory support system 10 to function as described herein, including, for example and without limitation, veno-venous (VV) connections and veno-arterial (VA) connections.

The controller 20 is communicatively coupled to the blood pump assembly 14, and is configured to control operation thereof. For example, the controller 20 is configured to control operation (e.g., a speed) of the blood pump 24. The controller 20 can generally include any suitable computer and/or other processing unit, including any suitable combination of computers, processing units and/or the like that may be communicatively coupled to one another (e.g., controller 20 can form all or part of a controller network). Thus, controller 20 can include one or more processor(s) and associated memory device(s) configured to perform a variety of computer-implemented functions (e.g., performing the methods, steps, calculations and/or the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit (ASIC), a digital signal processor (DSP), a field programmable gate array (FPGA), and other programmable circuits. Additionally, the memory device(s) of controller 20 may generally include memory element(s) including, but not limited to, non-transitory computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) can generally be configured to store suitable computer-readable instructions that, when implemented by the processor(s), configure the controller 20 to perform various functions including, but not limited to, controlling components of the blood pump assembly 14 as described herein.

The power supply 22 provides power to the blood pump 24, controller 20, and other electrical components of the blood pump assembly 14, and may generally include any suitable power supply that enables the extracorporeal mechanical circulatory support system 10 to function as described herein. While the controller 20 and power supply are illustrated as being external to the blood pump assembly 14, all or part of the controller 20 and/or the power supply 22 may be incorporated within the blood pump assembly 14 in other embodiments.

Figure 2:
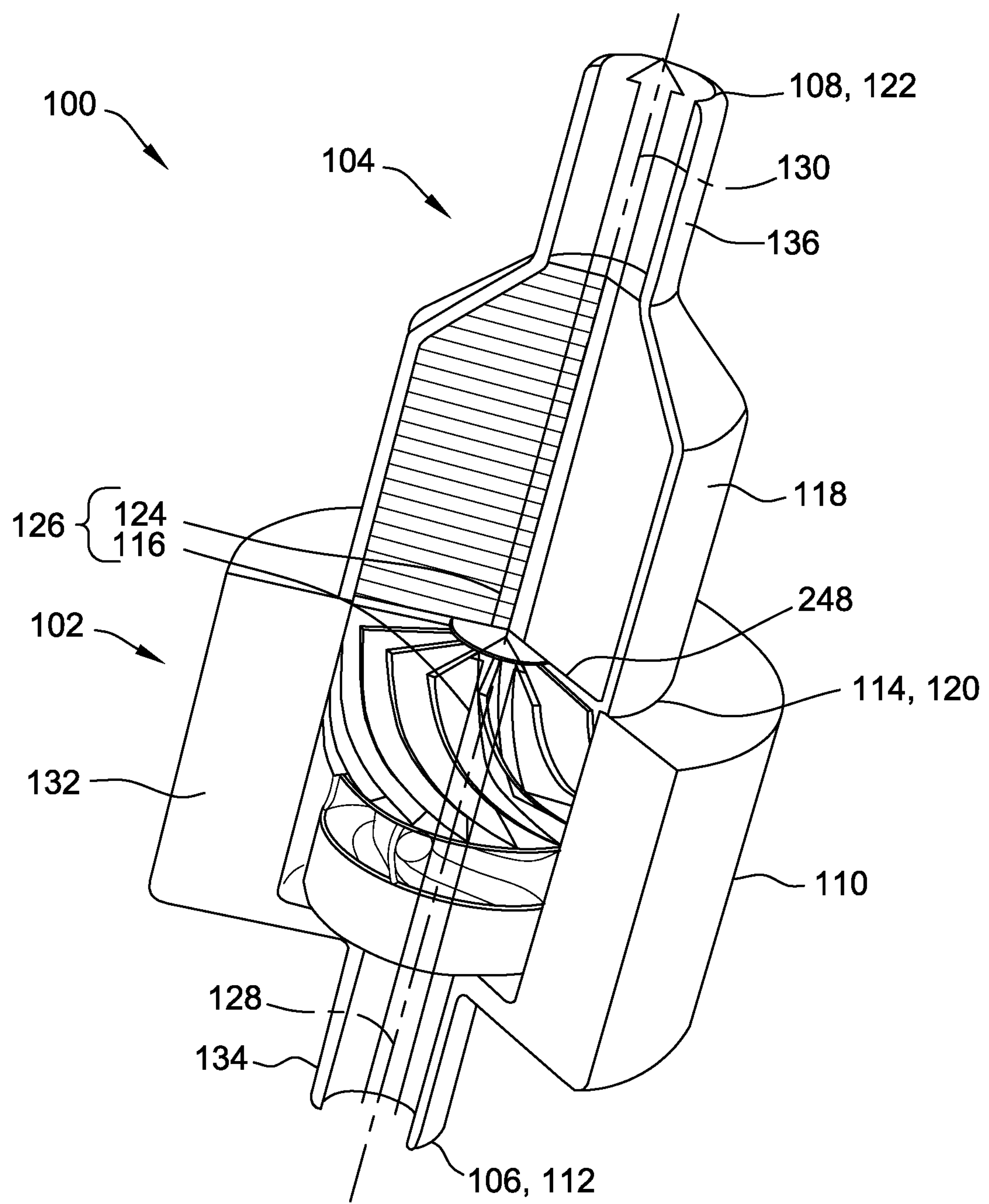
FIG. 2 is a perspective cut-away view of an extracorporeal blood pump assembly suitable for use in the mechanical circulatory support system of FIG. 1.

FIG. 2 is a perspective cut-away view of an exemplary extracorporeal blood pump assembly 100 suitable for use in the mechanical circulatory support system 10 shown in FIG. 1. The blood pump assembly 100 includes a blood pump 102 and an extracorporeal membrane oxygenator (ECMO) 104 fluidly connected to the blood pump 102. The blood pump assembly 100 includes an inlet 106 for receiving blood from a patient's circulatory system, and an outlet 108 for delivering blood back to the patient's circulatory system. The inlet 106 and outlet 108 may be fluidly connected to a patient's circulatory system using suitable fluid conduits (e.g., fluid conduits 16, 18, shown in FIG. 1), such as medical plastic tubing.

The blood pump assembly 100 is configured to pump blood from a patient's circulatory system such that blood is received at the inlet 106, pumped through the ECMO 104 to increase the oxygen concentration and/or decrease the carbon dioxide concentration in the blood, and pumped out of outlet 108 back into the patient's circulatory system. In the illustrated embodiment, the ECMO 104 is fluidly connected downstream of the blood pump 102 and defines the outlet 108, while the blood pump 102 defines the inlet 106. In other embodiments, the ECMO 104 can be fluidly connected upstream of the blood pump 102. Further, in the exemplary embodiment, the ECMO 104 is removably connected to the blood pump 102. That is, the blood pump 102 and the ECMO 104 are joined together in a non-permanent manner so as to allow the blood pump 102 and ECMO 104 to be repeatedly joined and separated without damage. The blood pump 102 and ECMO 104 may be removably connected to one another by any suitable non-permanent connecting means, including, for example and without limitation, threads, press-fit connectors, bayonet-type connectors, magnetic couplers, and combinations thereof. In other embodiments, the ECMO 104 may be non-removably connected to the blood pump 102, for example, by being integrally formed with the blood pump 102.

The blood pump 102 includes a pump housing 110 that defines an inlet 112, an outlet 114, and a blood flow path 116 extending therebetween. The ECMO 104 includes a membrane housing 118 that defines an inlet 120, an outlet 122, and a blood flow path 124 extending therebetween. The two blood flow paths 116, 124 cooperatively form a blood flow path 126 of the blood pump assembly 100 that extends from the blood pump assembly inlet 106 to the blood pump assembly outlet 108.

Figure 9:
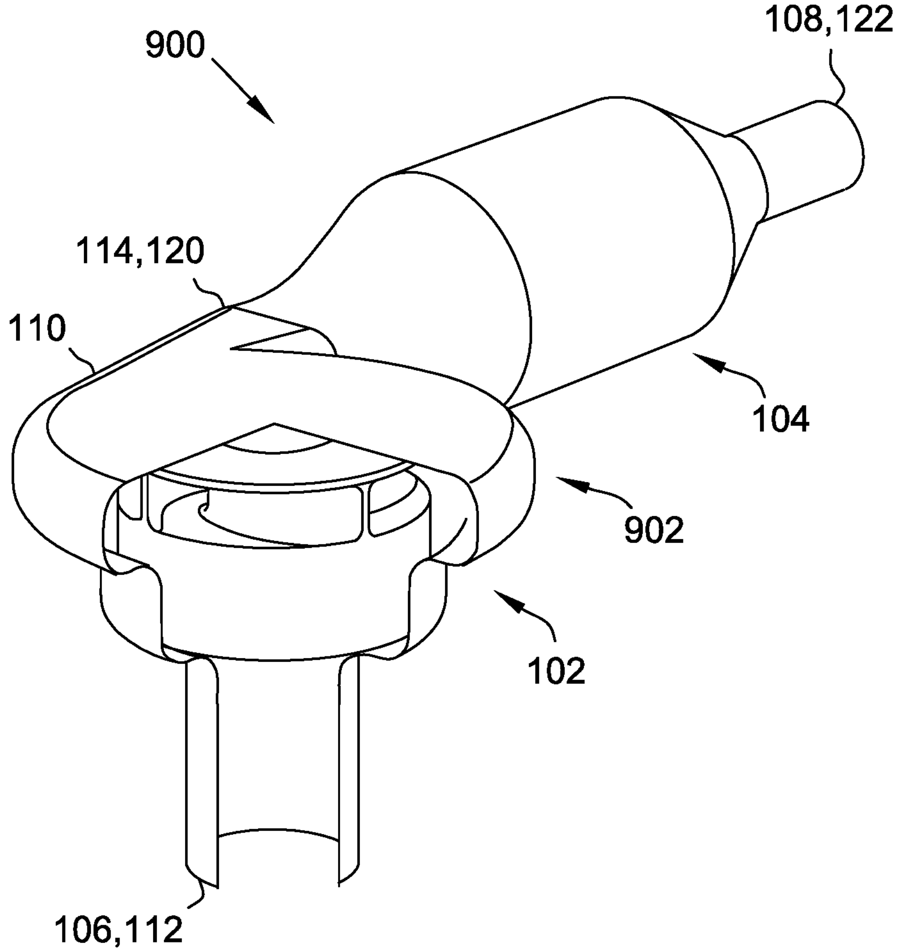
FIG. 9 is a perspective cut-away view of another extracorporeal blood pump assembly suitable for use in the mechanical circulatory support system of FIG. 1.

In the illustrated embodiment, the pump housing 110 and membrane housing 118 have "in-line" configurations. That is, the respective inlets and outlets of the pump housing 110 and membrane housing 118 are axially in-line with one another. More specifically, the pump housing 110 extends along a longitudinal axis 128, and each of the pump housing inlet 112 and the pump housing outlet 114 are co-axial with the pump housing longitudinal axis 128. Similarly, the membrane housing 118 extends along a longitudinal axis 130, and each of the membrane housing inlet 120 and the membrane housing outlet 122 are co-axial with the membrane housing longitudinal axis 130. Moreover, the blood pump assembly inlet 106 and the blood pump assembly outlet 108 are also in-line with one another. In other embodiments, the pump housing 110 and/or the membrane housing 118 may have a configuration other than an in-line configuration. For example, FIG. 9 is a perspective view of another exemplary extracorporeal blood pump assembly 900 suitable for use in the mechanical circulatory support system 10 shown in FIG. 1, where the blood pump assembly 900 has a non-axial configuration. More specifically, the blood pump housing 110 of this embodiment defines a volute 902 positioned fluidly downstream from the pump rotor that redirects blood flow in a direction perpendicular to the direction of flow at the pump housing inlet 112. As shown in FIG. 9, the pump housing inlet 112 and outlet 114 are axially offset from one another, as are the inlet 106 and outlet 108 of the blood pump assembly 900. Moreover, in this embodiment, the ECMO 104 is integrated with the pump housing outlet 114 to receive blood flow therefrom. In this embodiment, axial blood flow through the ECMO 104 is in an azimuthal or predominantly azimuthal direction to the pump 102.

Referring again to FIG. 2, in the illustrated embodiment, the pump housing inlet 112 defines the inlet 106 of the blood pump assembly 100, and the membrane housing outlet 122 defines the outlet 108 of the blood pump assembly 100. In other embodiments, the pump housing outlet 114 may define the outlet 108 of the blood pump assembly 100, and the membrane housing inlet 120 may define the inlet 106 of the blood pump assembly 100. In operation, the blood pump 102 pumps blood through the blood flow paths 116, 124 from the respective inlets 112, 120 to the respective outlets 114, 122. In the illustrated embodiment, the membrane housing 118 is connected to the blood pump 102 at the pump housing outlet 114. That is, the membrane housing inlet 120 is connected to the pump housing outlet 114. In other embodiments, the membrane housing 118 may be connected to the blood pump 102 at the pump housing inlet 112 (i.e., the membrane housing outlet 122 may be connected to the pump housing inlet 112).

In the illustrated embodiment, the pump housing 110 includes a cylindrical main body 132 and a fluid conduit connector 134 extending from the main body 132. The fluid conduit connector 134 is adapted (e.g., sized and shaped) for connection to a fluid conduit (e.g., fluid conduits 16, 18), such as conventional medical tubing used to transfer blood. The fluid conduit connector 134 may have any suitable configuration that enables a leak-free or leak-resistant connection between the pump housing 110 and a fluid conduit, including, for example and without limitation, a luer connector. The pump housing 110 includes a single fluid conduit connector 134 that defines the pump housing inlet 112 in the illustrated embodiment. In other embodiments, the pump housing 110 may include more than one fluid conduit connector 134 (e.g., one defining the pump housing inlet 112 and one defining the pump housing outlet 114), or the single fluid conduit connector 134 may be located at and define the pump housing outlet 114.

The membrane housing 118 also includes fluid a conduit connector 136 that defines the outlet 122 of the membrane housing 118 in the illustrated embodiment. In other embodiments, the membrane housing 118 may include more than one fluid conduit connector 136 (e.g., one defining the membrane housing inlet 120 and one defining the membrane housing outlet 122), or the single fluid conduit connector 136 may be located at and define the membrane housing inlet 120.

Figure 3:
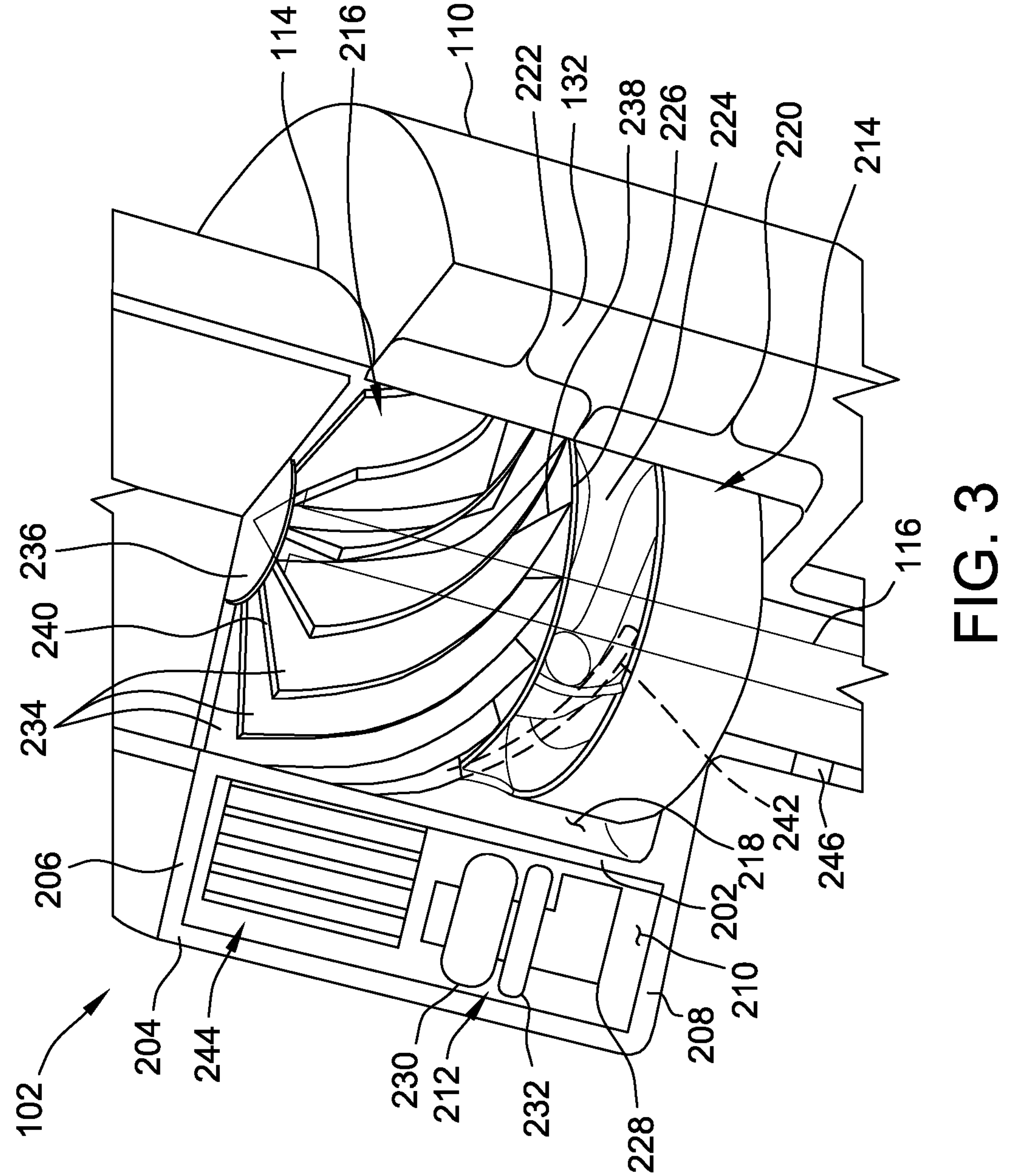
FIG. 3 is an enlarged view of a blood pump of the extracorporeal blood pump assembly of FIG. 2.

With additional reference to FIG. 3, the main body 132 of the pump housing 110 includes a radial inner wall 202, a radial outer wall 204 spaced radially-outward from the radial inner wall 202, a first end wall 206 extending between the radial inner wall 202 and the radial outer wall 204 adjacent the pump housing outlet 114, and a second end wall 208 extending between the radial inner wall 202 and the radial outer wall 204 adjacent the pump housing inlet 112. The pump housing 110 defines an internal cavity 210, separated from and sealed from the pump housing blood flow path 116, for housing electronics and other operational components of the blood pump 102. In the illustrated embodiment, the internal cavity 210 is defined by the radial inner wall 202, the radial outer wall 204, the first end wall 206, and the second end wall 208. The internal cavity 210 is separated from the blood flow path 116 by the radial inner wall 202.

The blood pump 102 further includes a stator 212 (shown schematically in FIG. 3), a rotor 214, and a flow converter 216. The stator 212 is positioned within the internal cavity 210, and the rotor 214 and the flow converter 216 are positioned within the pump housing blood flow path 116. The flow converter 216 is positioned fluidly downstream of the rotor 214 to convert non-axial flow (i.e., fluid flow primarily in a radial, azimuthal, and/or circumferential direction) from the rotor 214 to axial flow. Operation of the rotor 214 (i.e., rotation) causes fluid (e.g., blood) to flow through the blood flow path 116 from the inlet 112 (shown in FIG. 2) to the outlet 114. The pump housing 110 defines a rotor cavity 218 along a portion of the blood flow path 116 in which the rotor 214 and flow converter 216 are positioned. More specifically, the rotor cavity 218 includes an upstream portion 220 located proximate the pump housing inlet 112, and a downstream portion 222 positioned axially downstream of the upstream portion 220 and located proximate the pump housing outlet 114. The rotor 214 is positioned in the upstream portion 220 of the rotor cavity 218, and the flow converter 216 is positioned in the downstream portion 222 of the rotor cavity 218, axially downstream of the rotor 214.

The rotor 214 is operable to rotate in response to an electromagnetic field generated by the stator 212 to pump blood from the pump housing inlet 112 to the pump housing outlet 114. The stator 212 and rotor 214 may generally have any suitable configuration that enables the blood pump 102 to function as described herein. For example, the rotor 214 may be supported by one or more magnetic bearings, by one or more mechanical bearings, or any combination of magnetic and mechanical bearings. Suitable embodiments of stators and rotors are described, for example, in U.S. Pat. Nos. 7,798,952; 9,068,572; 9,091,271; and 9,265,870, the disclosures of which are hereby incorporated by reference in their entirety. In some embodiments, the rotor 214 is a magnetically levitated rotor having a configuration similar to that used in the CentriMag™ Acute Circulatory Support System commercially available from Abbott Laboratories.

In the illustrated embodiment, the rotor 214 defines a central aperture (not shown in FIG. 3) through which blood flows during operation of the blood pump 102. The rotor 214 includes impeller blades 224 and, in the illustrated embodiment, a shroud 226 that covers the downstream ends of the impeller blades 224 adjacent the flow converter 216. Additionally, in the illustrated embodiment, the rotor 214 includes a permanent magnet that defines the central aperture (not shown in FIG. 3). The permanent magnet has a permanent magnetic north pole and a permanent magnetic south pole for combined active and passive magnetic levitation of the rotor 214 and for rotation of the rotor 214. In operation, the stator 212 is controlled to drive (i.e., rotate) the rotor and to radially levitate the rotor 214 by generating electromagnetic fields that interact with the permanent magnetic poles of the permanent magnet. In this way, the stator 212 functions as an active magnetic bearing.

The stator 212 generally includes a plurality of winding structures that generate suitable electromagnetic fields that interact with the rotor 214 to cause rotor 214 to rotate and levitate. In the illustrated embodiment, the stator 212 includes a plurality of pole pieces 228 (one shown in FIG. 3) arranged circumferentially at intervals around the rotor cavity 218. The blood pump assembly 100 may include any suitable number of pole pieces that enables the blood pump assembly 100 to function as described herein. In some embodiments, the blood pump assembly 100 includes six pole pieces 228. In other embodiments, the blood pump assembly 100 can include more than or less than six pole pieces, such as four pole pieces or eight pole pieces. In yet other embodiments, the blood pump assembly 100 may include fewer than four pole pieces, or more than eight pole pieces. In the illustrated embodiment, each of the pole pieces 228 includes a drive coil 230 for generating an electromagnetic field to rotate the rotor 214, and a levitation coil 232 for generating an electromagnetic field to control the radial position of the rotor 214.

Each of the drive coils 230 and the levitation coils 232 includes multiple windings of a conductor wound around the pole pieces 228. The drive coils 230 and the levitation coils 232 of the stator 212 are arranged in opposing pairs and are controlled to drive the rotor 214 and to radially levitate the rotor 214 by generating electromagnetic fields that interact with the permanent magnetic poles of the permanent magnet. Although the drive coil 230 and levitation coil 232 are shown as separate coils in the illustrated embodiment, it should be understood that the drive coil 230 and levitation coil 232 may be implemented as a single coil configured to generate electromagnetic fields for both rotating and radially levitating the rotor 214. Suitable methods for controlling the stator 212 and generating electromagnetic fields to rotate and radially levitate the rotor 214 are described, for example, in U.S. Pat. Nos. 8,770,945; 9,068,572; and 9,849,224, the disclosures of which are hereby incorporated by reference in their entirety. The stator 212 may be coupled in communication with a suitable controller, such as the controller 20, to control the current supplied to the stator 212 to generate electromagnetic fields to rotate and radially levitate the rotor 214.

The flow converter 216 is positioned axially downstream of the rotor 214 in the illustrated embodiment, and is configured to convert non-axial blood flow from the rotor 214 into axial flow towards the pump housing outlet 114. The flow converter 216 may generally include any suitable structure for converting non-axial blood flow into axial blood flow, including, for example and without limitation, stator vanes, diffusers, volutes, and combinations thereof In the exemplary embodiment, the flow converter 216 includes a plurality of stator vanes 234 extending radially outward from a central hub 236. The stator vanes 234 and central hub 236 are positioned fluidly and axially downstream of the rotor 214, as shown in FIG. 3. Each stator vane 234 extends from a leading edge 238 to a trailing edge 240 along a path that gradually transitions from a primarily circumferential orientation to a primarily axial orientation. That is, each stator vane 234 extends from the leading edge 238 in a direction having a circumferential component and an axial component, where the circumferential component gradually and continuously decreases as the stator vane 234 extends towards the trailing edge 240 until the stator vane 234 is oriented substantially axially. The trailing edge 240 of each stator vane 234 is therefore circumferentially offset from the leading edge 238 by an angle. In the illustrated embodiment, the trailing edge 240 of each stator vane 234 is circumferentially offset from the leading edge 238 by an angle of about 30°. In other embodiments, the trailing edge 240 of each stator vane 234 may be circumferentially offset from the leading edge 238 by an angle less than or greater than 30°, such as 15°, 45°, 60°, 75°, or 90°.

In some embodiments, one or more of the stator vanes 234 may include a stator vane extension 242 that extends axially upstream of a downstream end of the rotor 214 (e.g., shroud 226) such that the stator vane extension 242 axially overlaps the rotor 214. The stator vane extension 242 may facilitate conversion of non-axial flow from the rotor 214 to axial flow by the flow converter 216. A single stator vane extension 242 is illustrated in broken lines in FIG. 3, though the plurality of stator vanes 234 can include more than one stator vane extension 242. In some embodiments, for example, each of the plurality of stator vanes 234 includes a stator vane extension 242.

In some embodiments, the flow converter 216 is removably connected to the pump housing 110, for example, to facilitate cleaning of the flow converter 216 and/or the pump housing 110 such that the blood pump 102 can be reused. For example, the stator vanes 234 and hub 236 may be connected to the pump housing 110 by a friction-fit or press-fit connection. Additionally or alternatively, the blood pump 102 may include one or more retaining rings (not shown in FIG. 3) connected to the pump housing at the upstream and/or downstream end of the stator vanes 234 to secure the stator vanes 234 and hub 236 in place. In yet other embodiments, the flow converter 216 is attached to the ECMO 104 (e.g., the membrane housing 118) and is inserted into the rotor cavity 218 when the membrane housing 118 is connected to the pump housing 110. In such embodiments, the flow converter 216 may be discarded when the ECMO 104 is replaced or discarded. In other embodiments, the flow converter 216 may be connected to the pump housing 110 using any suitable non-permanent connecting means that allows the flow converter 216 and the pump housing 110 to be repeatedly joined and separated without damage, including, for example and without limitation, threads, bayonet-type connectors, magnetic couplers, and combinations thereof. In other embodiments, the flow converter 216 may be non-removably connected to the pump housing 110. In some embodiments, for example, the stator vanes 234 and hub 236 may be formed integrally with the pump housing 110 (e.g., by additive manufacturing).

The blood pump assembly 100 also includes a heat exchanger 244 coupled in thermal communication with the flow converter 216 to heat and/or cool blood flowing through the blood pump assembly 100. The heat exchanger 244 may generally include any suitable heating and/or cooling elements that enable heat exchange with blood flowing through the blood pump assembly 100, including, for example and without limitation, resistive (e.g., electric) heaters, thermoelectric coolers (e.g., Peltier coolers), and fluid heat exchangers (e.g., heated or cooled water pumped through tubing in fluid communication with the plurality of stator vanes 234). In the embodiment illustrated in FIG. 3, the heat exchanger 244 is disposed within the internal cavity 210 and extends circumferentially around the plurality of stator vanes 234. The heat exchanger 244 is coupled in thermal communication with the plurality of stator vanes 234 through the radial inner wall 202 of the main body 132 such that heat is transferred between the heat exchanger 244 and the plurality of stator vanes 234 through the radial inner wall 202. In such embodiments, the main body 132 may be constructed of a suitable thermally-conductive material to facilitate heat exchange between the heat exchanger 244 and the plurality of stator vanes 234. Suitable thermally-conductive materials include, for example and without limitation, metals, metallic alloys, aluminum, titanium, steel, stainless steel, copper, brass, bronze, beryllium, any alloy combination thereof, and thermally conductive ceramics, such as alumina. The heat exchanger 244 is shown as being positioned proximate the flow converter 216 in FIG. 3, and extending an axial length approximately equal to that of the flow converter 216. In other embodiments, the heat exchanger 244 may extend axially beyond the flow converter 216 and/or may be positioned within the internal cavity 210 at a position other than proximate the flow converter 216. In some embodiments, for example, the heat exchanger 244 or a component thereof is positioned proximate the upstream portion 220 of the rotor cavity 218 to effect heat transfer proximate the rotor 214. Moreover, in some embodiments, the heat exchanger 244 may be partially or fully integrated with the radial inner wall 202. For example, the heat exchanger 244 may include one or more resistive heating coils that are molded, cast, embedded, or otherwise integrated within the radial inner wall 202. Additionally or alternatively, the heat exchanger 244 may include fluid channels defined by radial inner wall 202 for passage of a heat exchange fluid therethrough.

Figure 4:
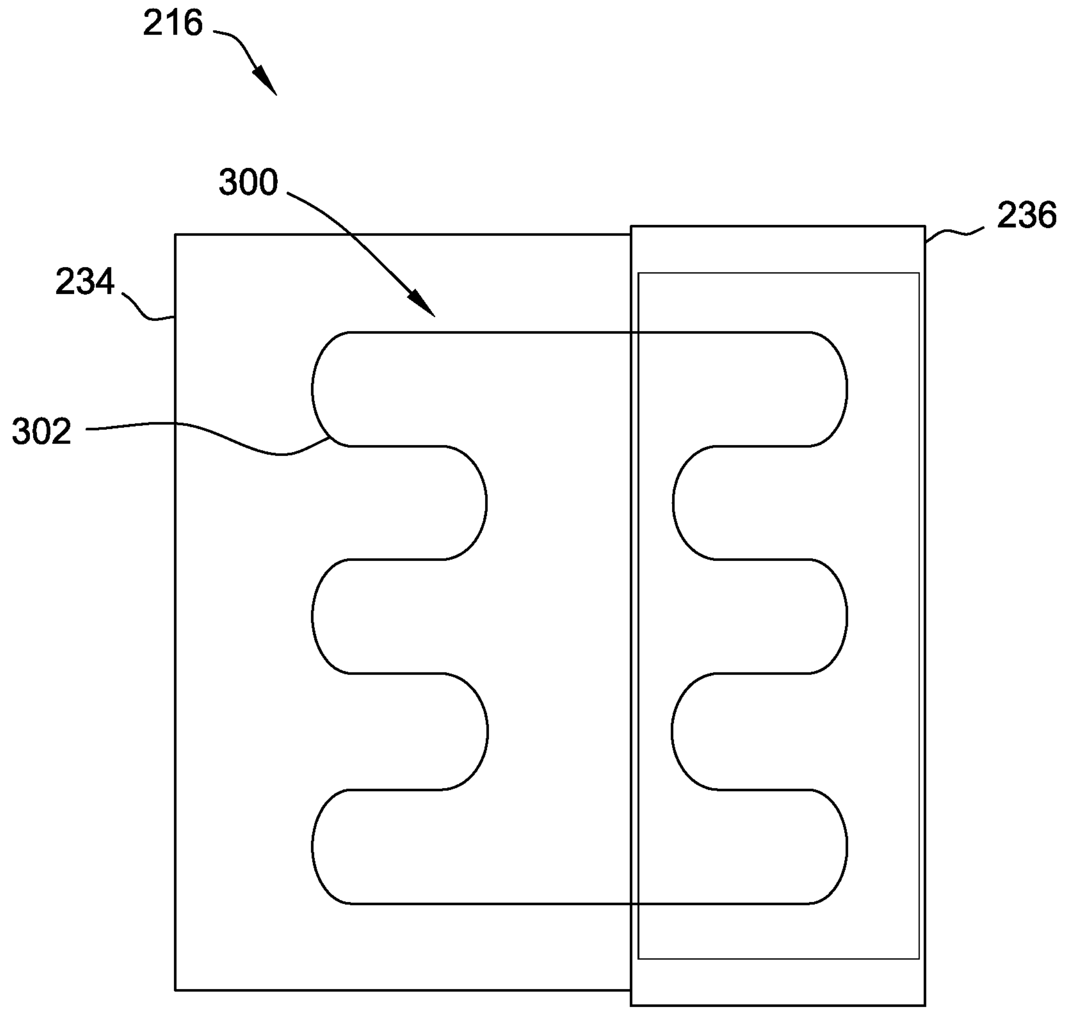
FIG. 4 is a schematic view of a portion of the blood pump of FIG. 3 including an example heat exchanger.

FIG. 4 schematically illustrates the flow converter 216 of FIG. 3 with another suitable embodiment of a heat exchanger 300 coupled in thermal communication with the flow converter 216. The heat exchanger 300 shown in FIG. 4 may be used in combination with or as an alternative to the heat exchanger 244 shown in FIG. 3. In this embodiment, the heat exchanger 300 is disposed within the central hub 236 and at least one of the plurality of stator vanes 234 (only one stator vane 234 illustrated in FIG. 4). More specifically, in this embodiment, the heat exchanger 300 is a resistive heater including at least one electrical wire 302 that is routed through the central hub 236 and at least one of the plurality of stator vanes 234. The electrical wire 302 is coupled to a suitable power source (e.g., power supply 22) for supplying power to the wire 302. Heat generated by the wire 302 through resistive heating is transferred to blood flowing through the blood pump assembly 100 through the stator vanes 234 and the central hub 236. In other embodiments, the heat exchanger 300 may not be disposed in the plurality of stator vanes 234, and may instead be disposed within the central hub 236. In such embodiments, heat exchange with blood flowing through the blood pump assembly 100 may occur through the central hub 236 and/or through the plurality of stator vanes 234 because the stator vanes 234 are coupled in thermal communication with the central hub 236. For example, heat generated within the central hub (e.g., by wire 302) may be thermally transferred to the plurality of stator vanes 234 by conduction, and subsequently transferred to blood through the stator vanes 234.

The blood pump 102 may include components other than those described above, including, for example and without limitation, an on-board controller and one or more sensors 246 for detecting characteristics of blood flow through the blood pump 102. In some embodiments, for example, an on-board or stand-alone controller is implemented as a printed circuit board (not shown in FIG. 3) positioned within the internal cavity 210, and is connected in communication with one or more sensors 246 to control operation of one or more components of the blood pump 102, such as the rotor 214 and the heat exchanger 244. The sensors 246 can include, for example and without limitation, pressure sensors, flow (volumetric and/or mass) sensors, and temperature sensors. Further, although a single sensor 246 is shown at the inlet 112 of the pump housing 110 in FIG. 3, it should be understood that the blood pump 102 may include any suitable number of sensors positioned at any suitable location(s) that enable the blood pump assembly 100 to function as described herein. In some embodiments, for example, the blood pump assembly 100 may include sensors 246 located at the pump housing inlet 112, the pump housing outlet 114, the membrane housing inlet 120, the membrane housing outlet 122, and/or at any location between the inlet 106 of the blood pump assembly 100 and the outlet 108 of the blood pump assembly 100, inclusive of the inlet 106 and outlet 108.

Figure 5:
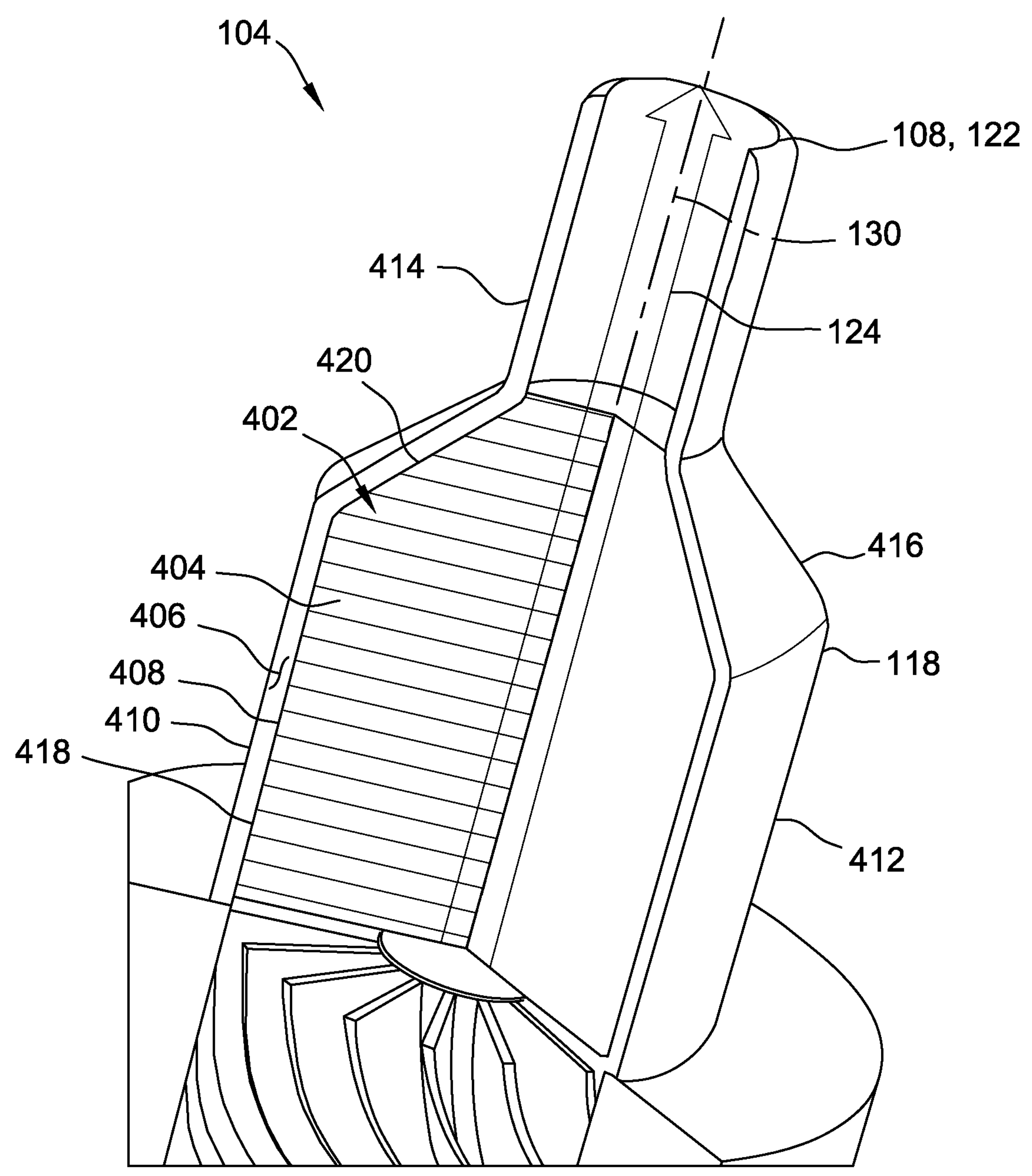
FIG. 5 is an enlarged view of an extracorporeal membrane oxygenator (ECMO) of the extracorporeal blood pump assembly of FIG. 2.

With additional reference to FIG. 5, the ECMO 104 includes an oxygenator membrane 402 to increase the oxygen concentration and/or decrease the carbon dioxide concentration of blood pumped through the blood pump assembly 100. The oxygenator membrane 402 is disposed within the blood flow path 124 defined by the membrane housing 118 such that blood flowing through the ECMO 104 flows through and contacts the oxygenator membrane 402. The oxygenator membrane 402 may generally include any suitable oxygenator membrane that enables the blood pump assembly 100 to function as described herein including, for example and without limitation, fiber bundles, porous media, stacked plates, micro-fluidic channels, bubble oxygenation, and artificially grown organs (e.g., lungs).

In the illustrated embodiment, the oxygenator membrane 402 is a fiber bundle that includes a plurality (e.g., thousands) of fibers 404, each configured for gaseous exchange with blood in contact therewith. In some embodiments, for example, the fibers 404 are hollow, microporous fibers that permit gas exchange with blood through micropores in the fibers. More specifically, each fiber defines an internal passage that is in communication with a gas source (e.g., oxygen and/or an oxygen-rich mixture of gases), and gas exchange is permitted between the gas within the internal passage and blood in contact with the fiber through micropores in the fiber surface. In other embodiments, the fibers 404 may be coated or skinned fibers that permit diffusion of oxygen and/or carbon dioxide through a non-porous skin layer on an outer surface of the fiber. The ends of the fibers 404 and/or fiber bundle may be cast potted (e.g., with a polymer, such as polyurethane). Additionally, the ends of the fibers may be trimmed, cut, or otherwise opened to permit communication between the internal passages of the hollow fibers and a gas source. Suitable fibers 404 for use in the oxygenator membrane 402 include, for example and without limitation, commercially available fibers having an outer diameter in the range of 200 to 400 microns, and a wall thickness in the range of 20 to 50 microns.

In the illustrated embodiment, gas is supplied to ends of the fibers 404 through a cavity 406 defined in the membrane housing 118. More specifically, the membrane housing 118 is a double-walled housing that includes an inner wall 408 and an outer wall 410 that cooperatively define the cavity 406. The cavity 406 is separated into a gas supply section and a vent section. The gas supply section is connected to a suitable gas source (e.g., oxygen and/or an oxygen-rich mixture of gases) that is supplied to fibers 404 for gaseous exchange with blood in contact therewith. The gas source can include, for example and without limitation, ambient atmosphere, compressed air, and oxygen. The vent section can be vented to atmosphere, or connected to a suitable rebreather system to facilitate drawing gas from the gas source through the fibers 404. A first end of each fiber 404 is disposed within the gas supply section of the cavity 406, and a second, opposite end of each fiber 404 is disposed in the vent section of the cavity 406 to allow gas from the gas source to flow through each fiber 404 from the gas supply section to the vent section.

Figure 6:
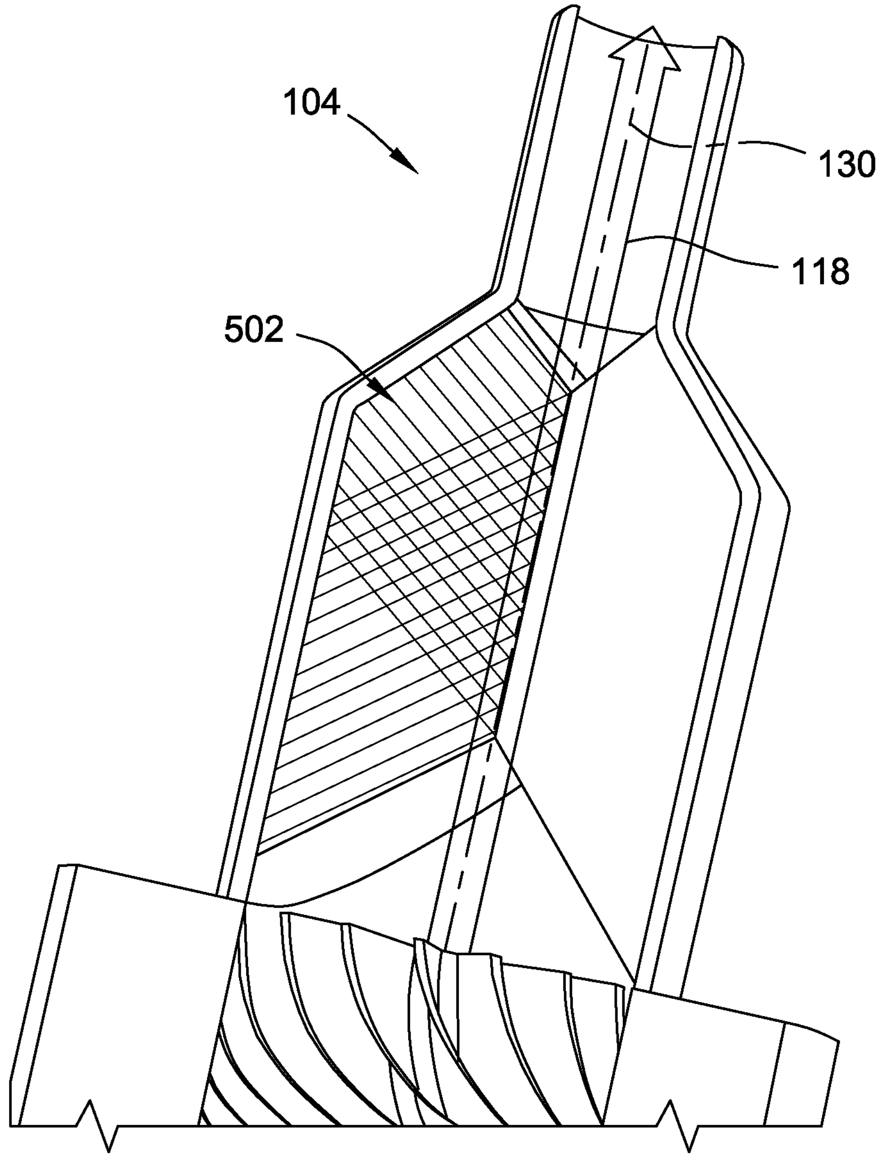
FIG. 6 is a cross-sectional view of the extracorporeal blood pump assembly of FIG. 2 including an ECMO with a multi-directional fiber oxygenator membrane.

In the illustrated embodiment, the fibers 404 of the fiber bundle are oriented perpendicular to the direction of blood flow, indicated by blood flow path 124, and the longitudinal axis 130 of the membrane housing 118. In other embodiments, the fibers 404 may be oriented at an orientation other than perpendicular to the direction of blood flow and/or the longitudinal axis 130 of the membrane housing 118. In some embodiments, for example, the fibers 404 are oriented parallel to the direction of blood flow and/or the longitudinal axis 130 of the membrane housing 118. In other embodiments, the fibers 404 may be oriented at an oblique angle relative to the direction of blood flow and/or the longitudinal axis 130 of the membrane housing 118. In yet other embodiments, the fibers 404 may have a multi-direction orientation. That is, the fiber bundle may include multiple sets of fibers 404, where each set of fibers is oriented at a different angle. FIG. 6, for example, illustrates the ECMO 104 with an oxygenator membrane 502 that includes a fiber bundle having a multi-direction orientation. In the illustrated embodiment, the fiber bundle includes two sets of fibers, each oriented at an approximate 45° angle relative to the direction of blood flow and the longitudinal axis 130 of the membrane housing 118. Without being bound by any particular theory, it is believed that such a fiber bundle orientation can facilitate reducing or breaking up microscopic flow patterns in blood flow through the membrane housing 118, and thereby facilitate improved oxygen and/or carbon dioxide transfer between the fibers 404 and blood flowing through the ECMO 104.

Referring again to FIG. 5, the membrane housing 118 includes a first section 412 having a first cross-sectional area, a second section 414 having a smaller cross-sectional area than the first cross-sectional area, and a third, tapered section 416 arranged between the first and second sections 412, 414 that has a tapering cross-sectional area. In the illustrated embodiment, the membrane housing 118 is generally cylindrical. More specifically, the first and second sections 412, 414 are cylindrical, and the third, tapered section 416 is frustoconical. Thus, in the illustrated embodiment, the first section 412 of the membrane housing has a first diameter, the second section 414 of the membrane housing 118 has a second diameter less than the first diameter, and the tapered section 416 has a diameter that transitions from the first diameter to the second diameter. In the illustrated embodiment, the tapered section 416 is located downstream from the first section 412 of the membrane housing 118, although in other embodiments, the tapered section 416 may be located upstream of the first section 412 of the membrane housing 118.

The oxygenator membrane 402 is disposed in the first section 412, and is generally sized and shaped complementary to the inner surface of membrane housing 118. In the illustrated embodiment, the oxygenator membrane 402 extends into the tapered section 416. Thus, in the illustrated embodiment, the oxygenator membrane 402 includes a first section 418 having a constant cross-sectional area or diameter, and a second section 420 having a tapering cross-sectional area or diameter. In the illustrated embodiment, fibers 404 in the fiber bundle are oriented perpendicular to the direction of blood flow and the longitudinal axis 130 of the membrane housing 118. Thus, fibers 404 positioned within the membrane housing tapered section 416 have a shorter length than fibers 404 positioned outside of the membrane housing tapered section 416 (i.e., fibers 404 positioned within the membrane housing first section 412). Without being bound by any particular theory, it is believed that fibers 404 positioned within the second, tapering section 420 of the oxygenator membrane 402, particularly fibers oriented perpendicular to or at an oblique angle to the direction of blood flow and the longitudinal axis of the membrane housing 118, may exhibit improved carbon dioxide transfer (i.e., removal) from blood as a result of the fibers 404 in the second, tapering section 420 having a smaller length, and therefore, a low carbon dioxide partial pressure across their entire length, as compared to other fibers 404 in the fiber bundle. Thus, ECMOs of the present disclosure may be optimized for both oxygen transfer and carbon dioxide transfer.

Figure 7:
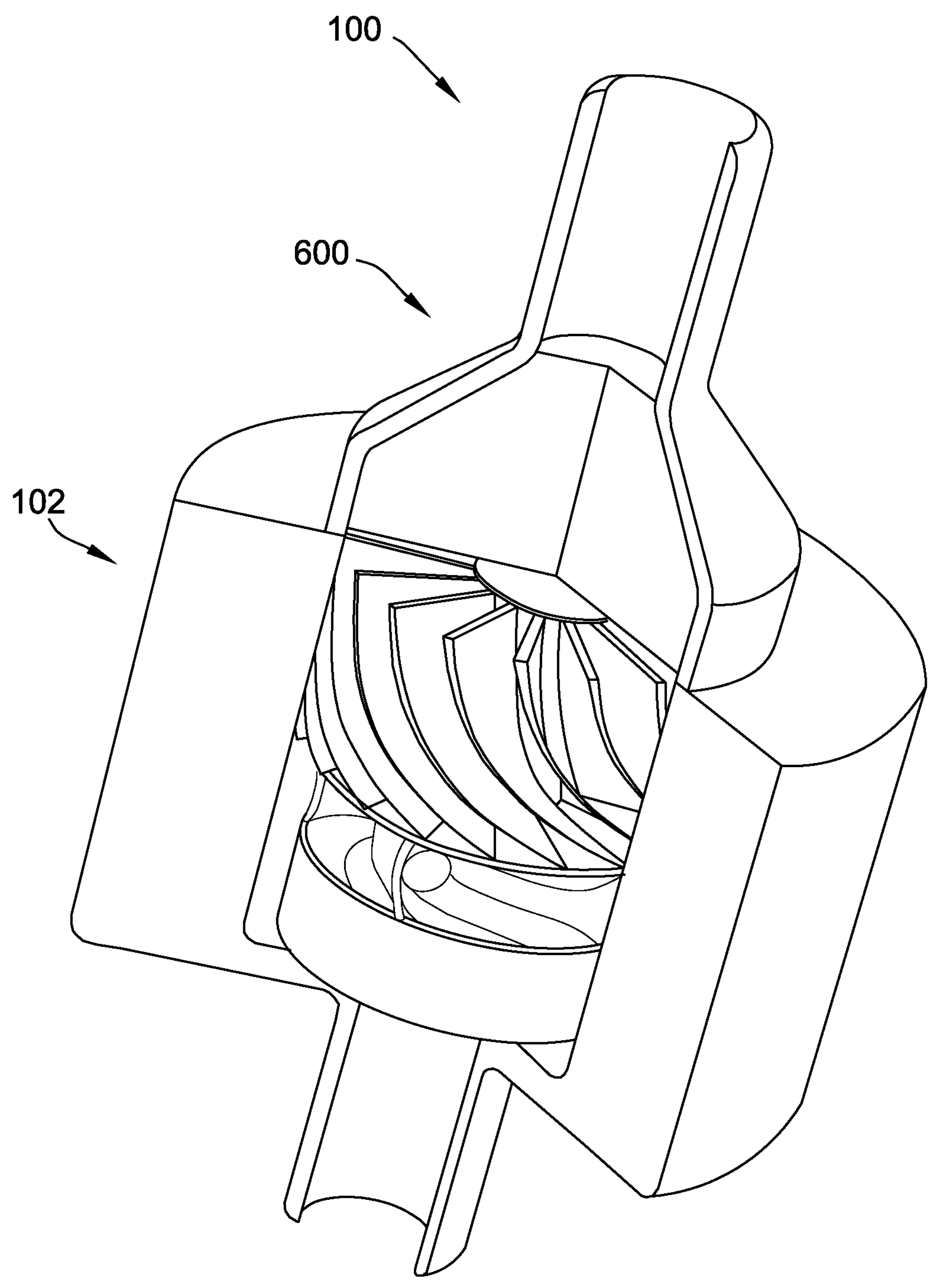
FIG. 7 is a perspective cut-away view of the extracorporeal blood pump assembly of FIG. 2 including a reduced-volume ECMO.

The ECMO 104 may have any suitable size and volume that enables the blood pump assembly 100 to function as described herein. In some embodiments, the size of the ECMO 104 is selected based on characteristics of the patient for which the blood pump assembly 100 is used. For example, a larger ECMO 104 may be used for an adult patient, whereas a smaller ECMO 600 (shown in FIG. 7) may be used for a child or pediatric patient. Additionally or alternatively, the ECMO 104 may be sized and shaped for optimal gas exchange characteristics. For example, an ECMO optimized for carbon dioxide removal (i.e., relatively long and narrow) may be used with a patients requiring enhanced carbon dioxide removal from blood. Moreover, the ECMO 104 may be interchangeable with different sized ECMOs, such as ECMOs having oxygenator membranes with a different oxygen and/or carbon-dioxide gas exchange capacity. In some embodiments, the ECMO 104 is one of a plurality of ECMOs configured for use with the blood pump 102. That is, the ECMO 104 may be part of a kit including the blood pump 102 and a plurality of ECMOs (e.g., ECMO 104 and ECMO 600), each interchangeable with one another and removably connectable to the blood pump 102. The ECMOs may have different sizes, volumes, and/or gas-exchange characteristics.

As noted above, the ECMO 104 and oxygenator membrane 402 of the illustrated embodiment have circular cross-sections. In other embodiments, the ECMO 104 and oxygenator membrane 402 may have cross-sections other than circular cross-sections. In some embodiments, for example, the ECMO 104 and oxygenator membrane 402 may have rectangular cross-sections. In such embodiments, blood flow through the blood pump assembly 100 would transition from a circular cross-section (i.e., within the pump housing 110) to a rectangular cross-section (i.e., within the membrane housing 118).

Figure 8:
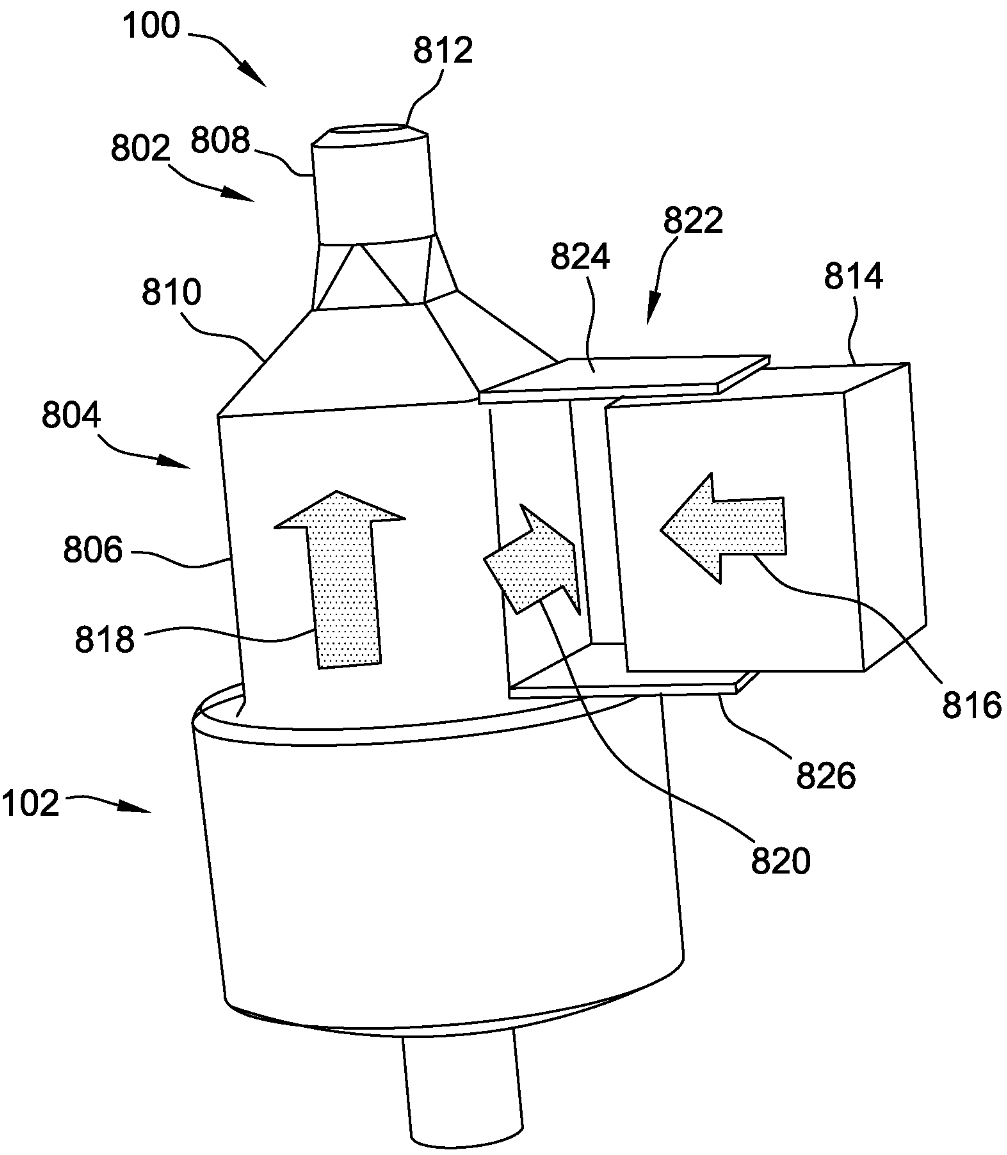
FIG. 8 is a perspective view of the extracorporeal blood pump assembly of FIG. 2 including an ECMO with a removable membrane cartridge.

FIG. 8 is a perspective view of the blood pump assembly 100 of FIG. 2 with an ECMO 802 having a rectangular cross-section. More specifically, the ECMO 802 of FIG. 8 includes a membrane housing 804 including a first section 806 having a rectangular cross-section, a second section 808 having a circular cross-section, and a third, tapered section 810 arranged between the first and second sections 806, 808 that has a frustopyramidal cross-section. The membrane housing first section 806 has a larger cross-sectional area than the membrane housing second section 808, and the membrane housing third section 810 has a tapering cross section that gradually decreases. In this embodiment, the membrane housing first section 806 defines an inlet (not shown in FIG. 8) of the ECMO 802, and the membrane housing second section 414 defines an outlet 812 of the ECMO 802.

In this embodiment, the oxygenator membrane (not labeled in FIG. 8) can be switched out "on the fly" or "hot swapped". More specifically, the oxygenator membrane is part of a membrane cartridge 814 that is insertable into and removable from the membrane housing 804 while the membrane housing 804 is connected to the blood pump housing 110. In other words, the membrane cartridge 814, which includes the oxygenator membrane disposed therein, can be inserted into and/or removed from the membrane housing 804 without disconnecting the membrane housing 804 from the blood pump housing 110. The membrane cartridge 814 is insertable into and removable from the membrane housing 804 in a direction (indicated by arrow 816) perpendicular to the direction of blood flow as well as the direction of gas flow through the fibers of the oxygenator membrane. In the illustrated embodiment, for example, blood flows through the blood pump assembly 100 in a first direction, indicated by arrow 818, and gas flows through fibers of the oxygenator membrane in a second direction, indicated by arrow 820, perpendicular to the first direction. The membrane cartridge 814 is insertable into and removable from the membrane housing 804 in the third direction 816 that is perpendicular to both the first direction 818 and the second direction 820.

In some embodiments, the ECMO 802 may include one or more mechanical guides 822 to facilitate insertion and/or removal of the membrane cartridge 814. Suitable mechanical guides 822 include, for example and without limitation, rails, plates, and combinations thereof. In the illustrated embodiment, the mechanical guides 822 include an upper plate 824 and a lower plate 826 connected to the membrane housing 804. The upper and lower plates 824, 826 extend from the membrane housing 804 to facilitate inserting the membrane cartridge 814 into the membrane housing 804. The upper and lower plates 824, 826 may be hingedly coupled to the membrane housing 804 to allow the plates to fold up into a collapsed configuration (i.e., against the membrane housing 804) when not in use.

Additionally, in some embodiments, the membrane cartridge 814 can be primed (i.e., filled with fluid) prior to insertion into the membrane housing 804. The mechanical guides 822 used to guide the membrane cartridge 814 into the membrane housing 804 may be configured to inhibit fluid from leaking out of the primed membrane cartridge 814. In the illustrated embodiment, for example, the upper plate 824 covers an outlet of the membrane cartridge 814, and the lower plate 826 covers an inlet of the membrane cartridge 814, thereby inhibiting fluid from leaking out of the membrane cartridge 814. Moreover, in some embodiments, fluid inlets and/or outlets may be integrated within the mechanical guides 822 to enable priming of the membrane cartridge 814. In the illustrated embodiment, for example, the lower plate 826 may include a fluid supply port that fluidly connects to the fluid inlet of the membrane cartridge 814 to supply fluid to the membrane cartridge 814 prior to insertion into the membrane housing 804. The upper plate 824 may include a fluid outlet, return line, and/or vent to facilitate pumping fluid through the membrane cartridge 814 to prime the membrane cartridge 814.

Referring again to FIG. 2, the membrane housing 118 and pump housing 110, when connected together, define a continuous blood flow path having a substantially constant cross-sectional area or diameter. More specifically, the membrane housing 118 is connected to the pump housing 110 at an interface 248 through which the blood flow path 126 of the blood pump assembly 100 extends. The cross-sectional area of the blood flow path 126 across the interface 248 is substantially constant. In the illustrated embodiment, for example, the cross-sectional area of the blood flow path 126 upstream of the interface 248 (i.e., the portion of the blood flow path 126 defined by the pump housing 110) is equal to the cross-sectional area of the blood flow path 126 downstream of the interface 248 (i.e., the portion of the blood flow path 126 defined by the membrane housing 118). Stated another way, the cross-sectional area of the membrane housing first section 412 is substantially equal to the cross-sectional area of the rotor cavity 218. In other embodiments, the cross-sectional area of the blood flow path 126 across the interface changes by less the 20%, by less than 10%, by less than 5%, or even by less than 2%. Additionally, the blood flow path 126 of the blood pump assembly 100 may be free of turns and bends to reduce shear stress and/or hemolysis of blood flowing through the blood pump assembly 100. In the illustrated embodiment, for example, the blood pump assembly inlet 106 and outlet 108 are axially in-line with one another, and the blood flow path 126 of the blood pump assembly 100 is free of bends and turns.

As described herein, the blood pump assemblies of the present disclosure provide several advantages over previous extracorporeal blood pump designs. For example, blood pump assemblies of the present disclosure facilitate reducing drops in blood pressure as compared, for example, to separate or standalone blood pump and ECMO modules, by providing a blood flow path that is free of bends and turns and that has a substantially constant cross-sectional area through the blood pump and the ECMO. This reduces or eliminates the nozzle/throat effect that otherwise results from connecting separate blood pump and ECMO modules with a piece of tubing, and also avoids unnecessary bends and twists in the blood flow path. Embodiments of the blood pump assemblies may also be free of volutes, which might otherwise cause a nozzle/throat effect, a longer than necessary blood flow path (and associated pressure drop and larger priming volume), and at least one extra bend in the blood flow path. Blood pump assemblies of the present disclosure also facilitate reducing the priming volume of the unit, for example, by eliminating tubing between the blood pump and the ECMO module and by providing modularity for different sized ECMO modules (e.g., ECMO modules for adult and pediatric modules with different priming volumes can be interchanged, as needed). The modularity of the blood pump assemblies also allows the oxygenator membrane of the ECMO to be replaced or discarded without having to discard the blood pump, allowing the blood pump to be cleaned and reused. Embodiments of the blood pump assemblies may also include an integrated heat exchanger, thereby eliminating the need for a separate heat exchanger and associated fluid lines (e.g., to connect separate water heater/water cooler).

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An extracorporeal blood pump assembly comprising:

a blood pump including a pump housing defining an inner cavity that houses a rotor and a flow converter positioned downstream from the rotor to convert non-axial flow from the rotor to axial flow, the pump housing defining a pump housing inlet and a pump housing outlet, the pump housing outlet corresponding to an outlet of the inner cavity; and an extracorporeal membrane oxygenator (ECMO) including a membrane housing and an oxygenator membrane disposed within the membrane housing, wherein the membrane housing defines a membrane housing inlet and a membrane housing outlet, wherein the blood pump housing and the membrane housing cooperatively define a blood flow path extending from i) an inlet of the blood pump assembly at the pump housing inlet to ii) an outlet of the blood pump assembly at the membrane housing outlet, wherein the pump housing inlet and the membrane housing outlet are axially in-line with one another and the pump housing outlet and the membrane housing inlet are axially in-line with another and connected at an interface, the blood flow path extending continuously and with a substantially constant cross-sectional area from the inner cavity of the pump housing and across the interface into the membrane housing.

2. The extracorporeal blood pump assembly of claim 1, wherein the blood flow path is free of bends and turns.

3. The extracorporeal blood pump assembly of claim 1, wherein the cross-sectional area of the blood flow path across the interface changes by less than 20%.

4. The extracorporeal blood pump assembly of claim 1, wherein the inner cavity includes an upstream portion and a downstream portion positioned axially downstream of the upstream portion, wherein the rotor is positioned in the upstream portion and the flow converter is positioned in the downstream portion.

5. The extracorporeal blood pump assembly of claim 1, wherein the flow converter includes a plurality of stator vanes positioned fluidly downstream of the rotor.

6. The extracorporeal blood pump assembly of claim 5, wherein at least one of the plurality of stator vanes includes a stator vane extension that extends axially upstream of a downstream end of the rotor such that the stator vane extension axially overlaps the rotor.

7. The extracorporeal blood pump assembly of claim 5, further comprising a heat exchanger, wherein the heat exchanger is at least one of coupled in thermal communication with the plurality of stator vanes or disposed within at least one of the plurality of stator vanes.

8. The extracorporeal blood pump assembly of claim 7, wherein each of the plurality of stator vanes extends radially outward from a hub, and wherein the heat exchanger is disposed within the hub.

9. The extracorporeal blood pump assembly of claim 7, wherein the heat exchanger is disposed within at least one of the plurality of stator vanes.

10. The extracorporeal blood pump assembly of claim 7, wherein the heat exchanger comprises at least one of a resistive heater and a thermoelectric cooler.

11. The extracorporeal blood pump assembly of claim 1, wherein the membrane housing includes a first section having a first cross-sectional area, a second section having a second cross-sectional area less than the first section, and a tapered section arranged between the first section and the second section and having a tapering cross-sectional area, wherein the oxygenator membrane is disposed in the first section and extends into the tapered section.

12. The extracorporeal blood pump assembly of claim 11, wherein the oxygenator membrane comprises a plurality of fibers, and wherein the fibers positioned within the tapered section have a shorter length than fibers positioned outside of the tapered section.

13. The extracorporeal blood pump assembly of claim 1, wherein the ECMO further comprises a membrane cartridge, wherein the oxygenator membrane is disposed within the membrane cartridge, wherein the membrane cartridge is insertable into and removable from the membrane housing while the pump housing is connected to the membrane housing.

14. An extracorporeal blood pump assembly kit comprising:

a blood pump including a pump housing defining an inner cavity that houses a rotor and a flow converter positioned downstream from the rotor to convert non-axial flow from the rotor to axial flow, the pump housing defining a pump housing inlet and a pump housing outlet, the pump housing outlet corresponding to an outlet of the inner cavity;

a first extracorporeal membrane oxygenator (ECMO) including a membrane housing defining a membrane housing inlet and a membrane housing outlet, wherein the membrane housing inlet of the first ECMO is removably connectable to the pump housing outlet such that the pump housing inlet is axially in-line with the membrane housing outlet, and wherein the pump housing outlet is axially in-line with the membrane housing inlet and connected to the membrane housing inlet at an interface, such that a blood flow path extends continuously and with a substantially continuous cross-sectional area from the inner cavity of the pump housing and across the interface into the membrane housing; and a second ECMO removably connectable to the one of the pump housing inlet and the pump housing outlet such that the first ECMO is interchangeable with the second ECMO, wherein the second ECMO has at least one of a size, a volume, and a gas exchange characteristic different from the first ECMO.

15. The extracorporeal blood pump assembly kit of claim 14, wherein the first ECMO further comprises an oxygenator membrane disposed within the membrane housing.

16. A method of assembling an extracorporeal blood pump assembly comprising:

providing a blood pump including a pump housing defining an inner cavity that houses a rotor and a flow converter positioned downstream from the rotor to convert non-axial flow from the rotor to axial flow, wherein the pump housing defines a pump housing inlet and a pump housing outlet, the pump housing outlet corresponding to an outlet of the inner cavity;

providing an extracorporeal membrane oxygenator (ECMO) including a membrane housing and an oxygenator membrane disposed within the membrane housing, wherein the membrane housing defines a membrane housing inlet and a membrane housing outlet; and removably connecting the membrane housing to the pump housing outlet, wherein the blood pump housing and the membrane housing cooperatively define a blood flow path extending from i) an inlet of the blood pump assembly at the pump housing inlet to ii) an outlet of the blood pump assembly at the membrane housing outlet, wherein the pump housing inlet and the membrane housing outlet are axially in-line with one another and the pump housing outlet and the membrane housing inlet are axially in-line with another and connected at an interface, the blood flow path extending continuously and with a substantially constant cross-sectional area from the inner cavity of the pump housing and across the interface into the membrane housing.

17. The method of claim 16, wherein the ECMO is a first ECMO, the method further comprising:

disconnecting the membrane housing from the pump housing; and removably connecting a second ECMO to the pump housing at the one of the pump housing inlet and the pump housing outlet, wherein the second ECMO has at least one of a size, a volume, and a gas exchange characteristic different from the first ECMO.

18. The method of claim 16, further comprising:

connecting a first fluid conduit to the pump housing inlet; and connecting a second fluid conduit to the membrane housing outlet.

* * * * *